United States Patent [19]

Schorno

[11] 4,344,917
[45] Aug. 17, 1982

[54] SAMPLE INLET FOR ANALYSIS INSTRUMENT AND METHOD OF SAMPLE ANALYSIS

[75] Inventor: Karl S. Schorno, Bartlesville, Okla.

[73] Assignee: Phillips Petroleum Company, Bartlesville, Okla.

[21] Appl. No.: 218,337

[22] Filed: Dec. 19, 1980

[51] Int. Cl.³ .............................................. G01N 1/22
[52] U.S. Cl. ................................ 422/78; 23/230 PC; 23/232 R; 23/232 C; 73/23.1; 422/83; 422/103
[58] Field of Search .......... 23/230 PC, 230 A, 232 R, 23/232 E, 232 C; 422/78, 103, 83; 73/422, 23.1

[56] References Cited

U.S. PATENT DOCUMENTS

| | | | |
|---|---|---|---|
| 3,053,077 | 9/1962 | Tracht | 73/23 |
| 3,118,300 | 1/1964 | Jenkins | 73/23 |
| 3,205,701 | 9/1965 | Szonntagh | 73/23.1 |
| 3,304,159 | 2/1967 | Hinsvark | 23/230 |
| 3,327,520 | 6/1967 | Stapp | 73/23.1 |
| 3,366,149 | 1/1968 | Taft | 141/82 |
| 3,463,012 | 10/1969 | McKinney | 73/422 |
| 3,482,450 | 12/1969 | Harris | 73/422 |
| 3,498,107 | 3/1970 | Kim | 73/23.1 |
| 3,518,059 | 6/1970 | Levy | 23/232 |
| 3,592,046 | 7/1971 | Cramers | 73/23.1 |
| 3,592,064 | 7/1971 | Gether | 73/422 |
| 4,035,168 | 7/1977 | Jennings | 55/67 |
| 4,084,440 | 4/1978 | Carpenter | 73/422 |
| 4,153,415 | 5/1979 | Espitalie | 23/230 |
| 4,159,894 | 7/1979 | Hu | 23/230 |

FOREIGN PATENT DOCUMENTS 2049178 12/1980 United Kingdom .

OTHER PUBLICATIONS

Van De Meen et al., Pyrolysis . . . , Geochim. Cosmochim. Acta 44, 999–1013 (1980).
*Claypool*, Thermal–Analysis Technique for Source-Rock Evaluation, Amer. Assoc. Petr. Geol. Bull., vol. 60, pp. 608–612 (1976).
*Barker*, Pyrolysis Techniques for Source-Rock Evaluation, Amer. Assoc. Petr. Geol. Bull., pp. 2349–2361 (1974).
*Welte*, Hydrocarbon Source Rocks in Deep Sea Sediments (1979).
*Espitalie*, Source Rock Characterization Method for Petroleum Exploration.
*Giraud*, Application of Pyrolysis and Gas Chromatography to Geochemical, Characterization, Amer. Assoc. Petr. Geol. Bull., vol. 54, pp. 439–455 (1970).

*Primary Examiner*—Ronald E. Serwin

[57] ABSTRACT

A sample injection system for a gas chromatograph or other analysis instrument is described. The sample injection system can be used in conventional gas chromatographs containing a detecting device and an internal heat source to provide temperature-programming capability for analyses involving thermal extraction of hydrocarbons and other gaseous products from a solid or liquid sample. The injection system includes a sample chamber having a sample inlet and an outlet, means to control the temperature of the sample chamber, a carrier gas inlet to the sample chamber, and means defining a flow path extending from the sample chamber outlet and for absorbing heat from the internal heat source. A method for analyzing geological samples to determine certain petroleum-related characteristics is also described.

23 Claims, 7 Drawing Figures

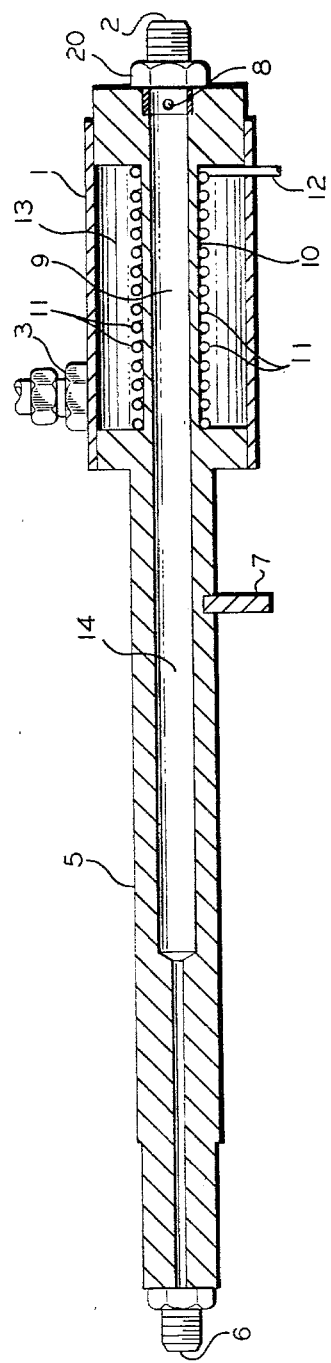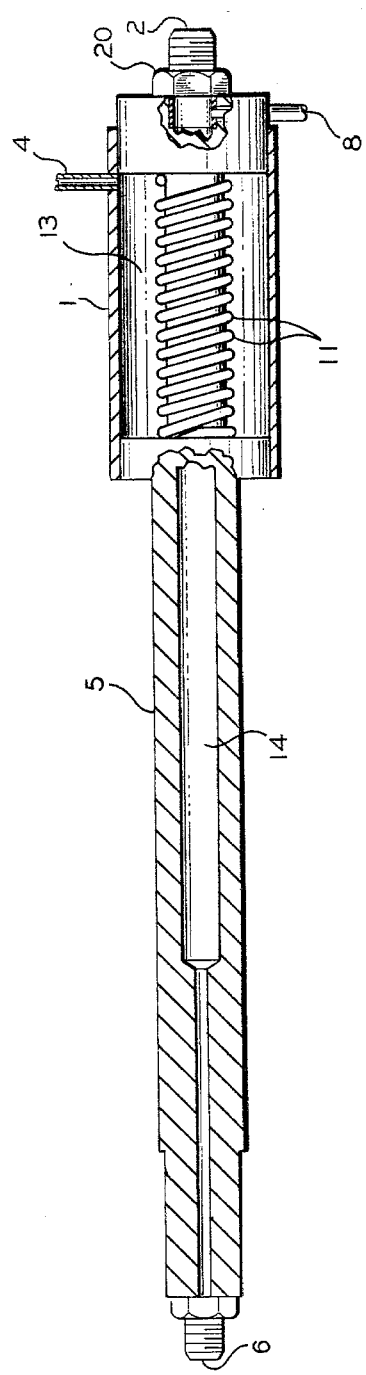
FIG. 3
FIG. 4

SAMPLE INLET FOR ANALYSIS INSTRUMENT AND METHOD OF SAMPLE ANALYSIS

BACKGROUND OF THE INVENTION

This invention relates to a method and apparatus for the chemical analysis of matter. In one aspect, it relates to an injection system for a gas chromatograph or other analytical instrument. In another aspect, it relates to a method of analyzing geological samples to evaluate the petroleum-generating potential of the sample.

In the field of geochemical research and petroleum exploration, an area of growing interest is the analysis of geological samples to determine the remaining petroleum-generating potential of the rock sample. Work in this field has been directed to methods for removing hydrocarbons from geological samples and analyzing the hydrocarbons, to apparatus for laboratory and field analysis of geological samples, and to the development of theoretical and practical models for predicting petroleum-exploration-related characteristics from the raw data obtained. A method known in the art for such analyses involves the thermal extraction of volatile hydrocarbons from a kerogen (insoluble organic portion of sedimentary rocks) or rock sample under carefully controlled temperature conditions and the analysis of the hydrocarbons extracted. In this method, a geological sample is heated to about 300° C. at a constant rate of temperature increase. A gas detecting instrument records signals representative of the quantity of both volatile hydrocarbons and other gases thermally extracted from the sample. The sample is further heated to a higher temperature at a constant rate of temperature increase. A gas detecting instrument records signals representative of the quantity of hydrocarbons and inorganic gases formed by pyrolysis over some predetermined temperature range. The quantities of hydrocarbons formed can be expressed in units of milligrams hydrocarbon per gram sample. One such thermal method involves the controlled heating of a geological sample and the determination of the amounts of hydrocarbons and non-hydrocarbons generated over at least two predetermined temperature ranges. Products thus obtained are reported in units of milligrams of product per gram of rock. These quantities are in turn used to obtain thermal parameters which are used to "type" rock samples according to an established system for categorizing samples in terms of their geological maturity, organic source, and oil-generating potential. The hydrocarbon parameter can be derived mathematically from laboratory analyses which provide the quantity of hydrocarbons generated from a rock, the rock and the total organic carbon in the rock sample.

In performing thermal analyses of geological samples by such methods, it is important to be able to heat the sample to an accurately-determined temperature at a chosen rate of temperature increase. New pyrolysis instruments which are designed for controlled thermal extraction are commercially available but these are generally expensive. Most researchers who are interested in the above analysis have gas chromatography instruments which can perform the analysis of hydrocarbons but which are not capable of heating the sample at a uniform rate as required in the above thermal analysis method. It is thus an object of the invention to provide a universal injection system adapter for a gas chromatograph for thermal analyses.

It is a further object of the invention to provide an adapter for a gas chromatograph or other analytical instrument which provides additional temperature-programming capability to the instrument.

SUMMARY OF THE INVENTION

According to the invention, an adaper device for a gas chromatograph or other analytical instrument is provided comprising a first section and a second section, said first section including a sample chamber, means for heating the sample chamber including means for operatively associating the heating means to a temperature control means, a carrier gas inlet to the sample chamber, a sample inlet at one end of the sample chamber and an gas outlet at the opposite end of the sample chamber, and the second section comprising means for defining a gas flow path and for absorbing heat from an exterior heat source thereby preventing gas condensation in the gas flow path, the gas flow path extending openly from the sample chamber outlet. According to a preferred embodiment the first section also includes means for cooling the sample chamber such as an annular space for cooling gas flow in indirect heat exchange with the sample chamber, the annular space being defined by the sample chamber exterior and a jacket surrounding and spaced apart from the sample chamber. The adapter device may be fitted with a securing means such as a guide pin which can also be used to secure the device to the analytical instrument.

Further according to the invention, an adapter for a gas chromatograph or other analytical instrument is provided comprising at least one rigid tube having a first portion and a second portion, one end of the tube providing a sample inlet into a sample chamber and the opposite end of the tube providing an outlet having a smaller diameter than the sample inlet. If the adapter comprises more than a single continuous length of tubing, the plurality of tubular members are adjoined so as to provide a continuous linear flow path therethrough, which flow path may vary in diameter from the sample inlet to the opposing outlet. The first portion of the tube, defining the sample chamber, is surrounded by a jacket spaced apart from the tube and optionally containing means for admitting and removing a cooling fluid from an annular space between the tube and the jacket. A carrier gas inlet opens into the first portion of the tube, preferably in the sample inlet portion. The first tube portion is closely contacted along its exterior length by heating means and a temperature-sensing means such as a thermocouple, preferably in intimate contact with the first tube portion, through which a controller can be associated with the heating coil to provide temperature control. The second tube portion defines a flow path which extends from the outlet of the sample chamber to a gas outlet for the second tube portion. The second tube portion is of sufficient exterior radius to absorb heat from an exterior source and thereby prevent condensation of vapors in the flow path therein. The adapter device replaces a standard injector port for a gas chromatograph, the first tube portion optionally positioned exterior to a gas chromatograph oven and the second portion positioned within the gas chromatograph injector block or oven so as to draw heat therefrom.

BRIEF DESCRIPTION OF THE DRAWINGS

FIG. 3 is a cross-sectional view taken along lines 3—3 of FIG. 2.

FIG. 4 is a cross-sectional view taken along lines 4—4 of FIG. 1.

DETAILED DESCRIPTION OF THE INVENTION

The sample injection system of the invention is designed to be adaptable to a conventional gas chromatograph to make possible the thermal analysis of solid or liquid samples under controlled heating conditions. The invention sample injection system thus replaces the standard injection port of a gas chromatograph to adapt the instrument for certain types of thermal analyses. The injection system enables a solid or liquid sample to be purged with helium at cryogenic or higher temperature if desired, admitted to a gas chromatograph, and then heated at a uniform rate to effect the controlled thermal extraction, or pyro-extraction of volatile hydrocarbons and other gaseous products. A particular injection system can be adjusted so as to replace the injector on various commercially-available or custom-built gas chromatographs, thus providing an excellent pyrolysis instrument using available gas chromatography equipment and circumventing the necessity of a large expenditure for a separate pyrolysis unit specifically designed for such thermal analyses. The apparatus of the invention offers certain advantages over commercially available adapters for gas chromatographs, such as evenly-distributed, accurately-measurable heating of the sample chamber and a design which permits insertion of at least a part of the injector, including at least a major portion of the carrier stream conduit from the sample chamber to the detecting means, to be situated during use within the oven of the gas chromatograph, thereby eliminating the problem of vapor condensation which is inherent in adapters which are connected to a standard gas chromatograph inlet port via a thin, exposed tube extending from the heating chamber of the adapter outlet. One embodiment of the invention sample injection system also permits transfer of the sample itself from the adapter heating chamber to the gas chromatograph oven area, if desired.

The invention adapter device for a gas chromatograph can best be described by reference to FIGS. 1-4, which show a preferred embodiment of the adapter device.

Figure 1:
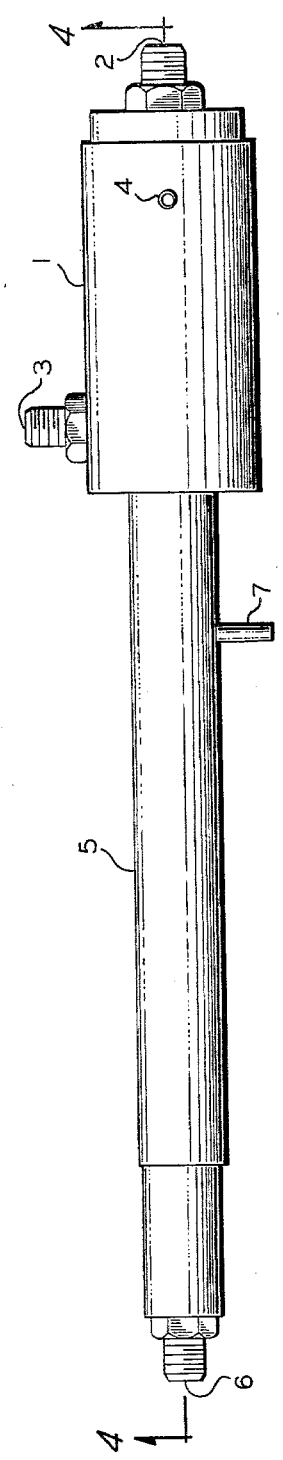
FIG. 1 is an elevation of one embodiment of the invention apparatus.
Figure 2:
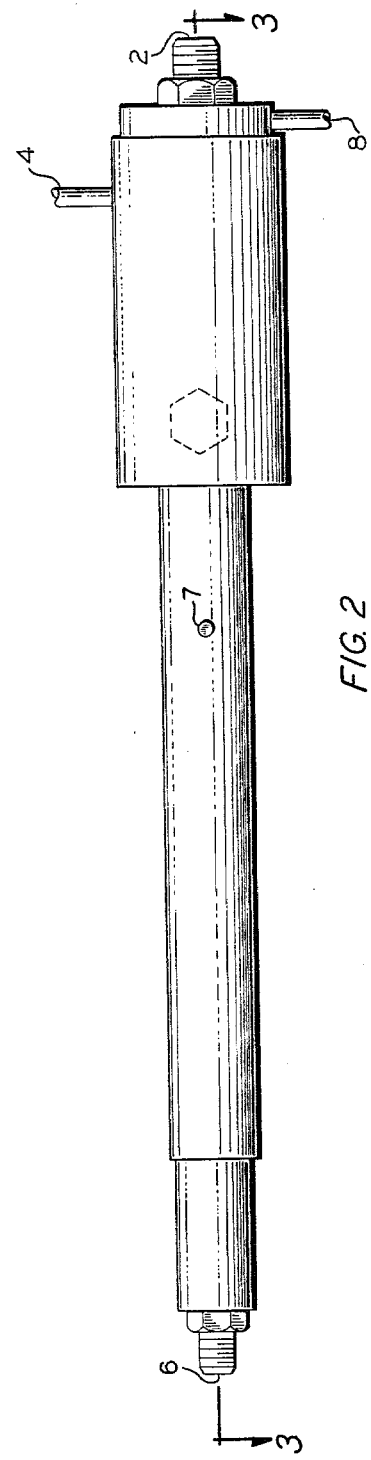
FIG. 2 is an elevation of the apparatus of FIG. 1 rotated 90° along the longitudinal axis.

FIGS. 1 and 2 show the structural exterior of an adapter device for use in a gas chromatograph instrument and for thermal analyses of geological samples. Jacket means 1 encloses a first portion of the adapter device, which first portion includes an interior sample chamber having sample inlet 2 and an annular space between the sample chamber and jacket 1. Cooling fluid inlet 3 opens into the annular space from a source (not shown) of cooling liquid or gas such as air, which can be introduced into the annular chamber to flow therethrough in indirect heat exchange with the sample chamber walls. Cooling fluid outlet 4 is provided in jacket 1 for removal of the cooling fluid from the annular space.

A second adapter portion 5 of the adapter device extends with a reduced diameter from the first portion and includes outlet 6 which is in direct flow communication with sample inlet 2. The outlet end portion of the adapter is shown having a gas-tight threaded receiving end for attachment of a flow connecting means to a detector device (not shown). Guide pin 7 provides means to position and secure the adapter device in a gas chromatograph having an inner recessed portion for receiving the guide pin.

FIGS. 3 and 4 illustrate in cross section the invention adapter device. Sample inlet 2 opens into sample chamber 9 within tube 10. Tube 10 is in contact with heating coils 11 which extend along the major portion of that length of tube 10 enclosed by jacket 1.

For most accurate control of the temperature in the sample chamber, the heating coils are preferably in intimate contact with the underlying tube and each coil is in close proximity to the adjacent heating coil. The best results have been obtained by high-temperature soldering the entire length of the heating coils to the underlying tube so as to maximize heat transfer and minimize air space between the heating coils and the tube.

The heating coil is connected via electrical conduit 12 to a power source (not shown) and is preferably associated with a multi-stage temperature-controlling device capable of controlling the temperature of the heating coil, multi-rates at which the temperature of the coil can be elevated, and multi-hold time for the initial temperature, between temperature increases, and final temperature hold.

Annular space 13 is defined by tube 10 and jacket 1 and contains cooling fluid inlet 3 and cooling fluid outlet 4 (as best seen in FIG. 3). The cooling fluid can be any suitable gas or liquid, preferably compressed air. Annular space 13 may contain baffle means for deflecting flow of the cooling fluid therein if increased cooling efficiency is desired.

Sample chamber 9 extends openly into the flow path within the longitudinally-extended second portion 5 of the adapter device. The flow path 14 may be equal to or smaller in diameter than the sample chamber diameter and may, as shown in FIGS. 3 and 4, open into a flow path of reduced diameter within the second portion of the adapter device. The tube defining flow path 14 is preferably a strong, rigid structure of a material which can absorb and transfer heat, such as stainless steel.

Figure 5:
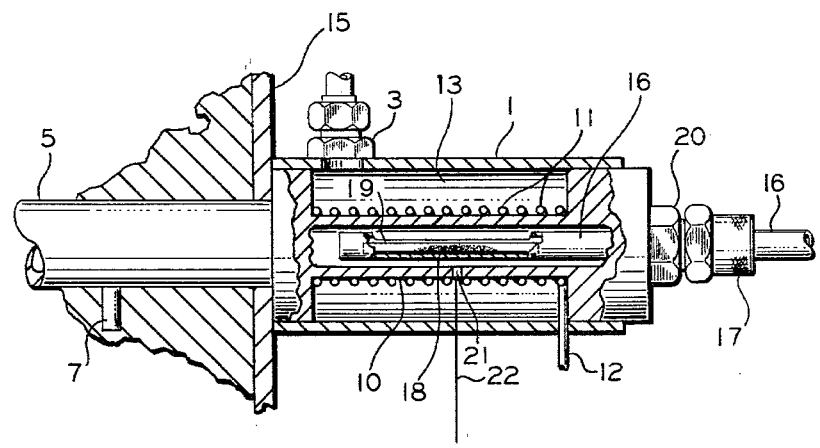
FIG. 5 is a cross-sectional view showing the adapter stationed in a pyrolysis unit, with a sample-containing insertion means fixed in place so that the sample is within the sample chamber.

FIG. 5 shows in cross section the adapter device positioned with respect to a gas chromatograph 15. It is understood that for analyses of the type contemplated, the gas chromatograph instrument includes at least one detecting device and a heat source or oven within the instrument enclosure for maintaining the proper operating temperature for the instrument.

In performing analyses using the adapter-modified gas chromatograph, an accurately-weighted sample to be analyzed is first placed in a suitable insertion means for placement within the sample chamber of the adapter. The sample can be a solid or a liquid. Such materials as rock, kerogen, polymer, coal, asphaltene and freeze-dried bacteria are examples of suitable types of sample material. The adapter is particularly suitable for use in a gas chromatograph for analyzing rock and kerogen samples under closely-controlled temperature conditions.

The sample can vary in size depending upon the instrument and the analysis to be performed, but a solid sample will generally range in weight from about 1 mg to about 100 mg. In FIG. 5, a rock sample 18 is shown within a sample tube 19 positioned within sample insertion means 16. The sample, in small granules or powder form, is conventionally placed in a quartz tube the ends of which are enclosed by gas-permeable quartz wool. The sample insertion means is shown locked in place with cap 17 over threaded fitting 20.

If desired prior to the heating operation, the sample can be contacted with a flowing carrier gas for a time effective for removing contaminants from the sample and from the insertion means and for allowing the detector response to stabilize. The carrier gas can be any suitable gas and is preferably an inert gas such as helium. During this initial step, a cooling fluid such as compressed air may be passed through annular space 13 for direct heat exchange with the sample chamber exterior 10 to maintain the temperature in the sample chamber at about 60° C. Cryogenic fluids can also be used to reduce this temperature.

Following this operation, air flow through annular space 13 is terminated and sample heating is initiated by activation of heating coil 11. The heating coil is associated via electrical connection 12 with a multi-stage temperature programmer such as a Theall Model 2200 Programmer, which is set to raise the temperature of the heating coils at a constant predetermined rate, which can vary from about 20° C./min to about 180° C./min. At a predetermined temperature, generally about 300° C. for rock sample analyses, the temperature is held constant for a time sufficient for the detector to respond to the hydrocarbons generated by the heating of the sample. Generated gases are swept by the carrier gas from the sample chamber through the flow path in adapter portion 5 and to a gas detecting means such as a flame ionization detector. The detector generates a signal representative of the quantity or quality of the hydrocarbons present in the carrier gas. The signal is amplified and recorded on a chart recorder in millivolts response per second or is converted to a DC signal and sent to a microprocessor for conversion into a weight hydrocarbon per grams of rock or carbon.

After the signal from the detector has stabilized, the temperature is again elevated by the heating coils in communication with the temperature programmer. The temperature is set to increase at a predetermined rate up to about 575° C., at which the temperature is again maintained to allow quantitative evaluation of the hydrocarbons generated. The sample chamber is cooled quickly back to the preselected initial temperature with a suitable coolant fluid via conduit 3.

Temperature control is regulated by thermocouple 21, which sends an electrical signal via conductor 22, which feeds a temperature readout and the temperature programmer. For most accurate control of the temperature of the sample, it is preferable that the thermocouple be in close contact with, preferably embedded in and soldered to the sample chamber tube prior to placement of the heating coil around the tube. The accurate reading of temperature at the sample and for calibration of the microprocessor controlling the oven heaters 11 can be accomplished by a calibrated thermocouple through conduit 16 to the sample 18.

An example of thermal analysis of a geological sample using the adapter device of the invention is given below.

EXAMPLE

Figure 6:
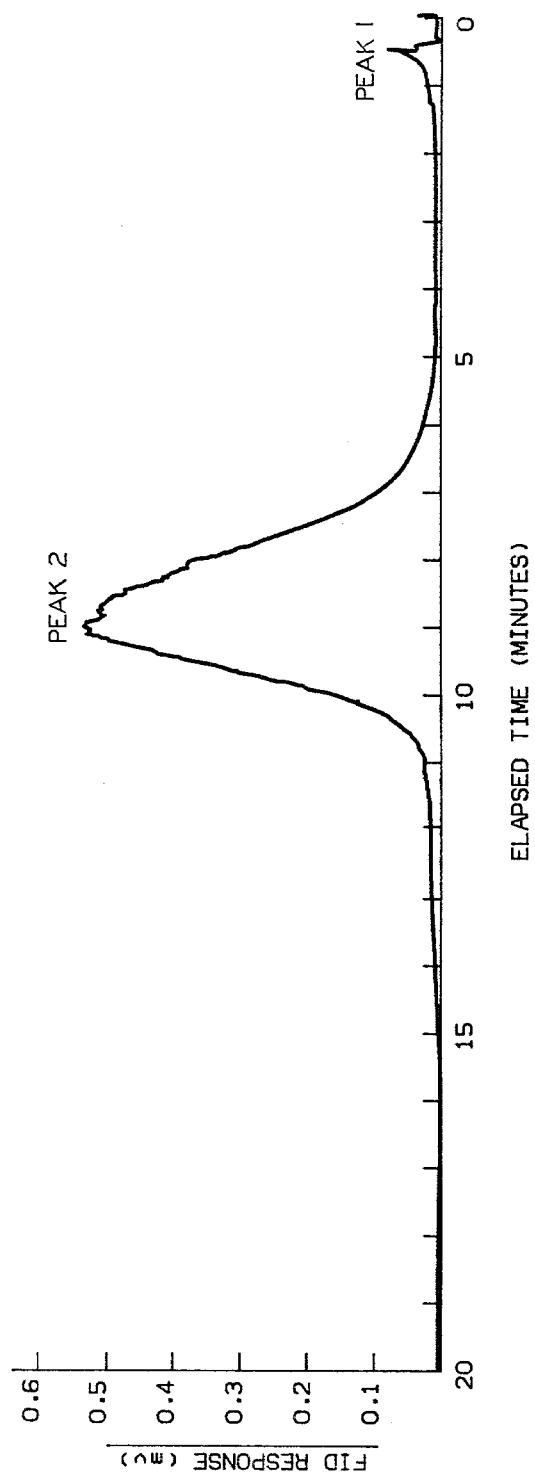
FIG. 6 is a pyrogram showing the charted results of a thermal analysis of a geological sample using the invention injection system and a flame ionization detector.
Figure 7:
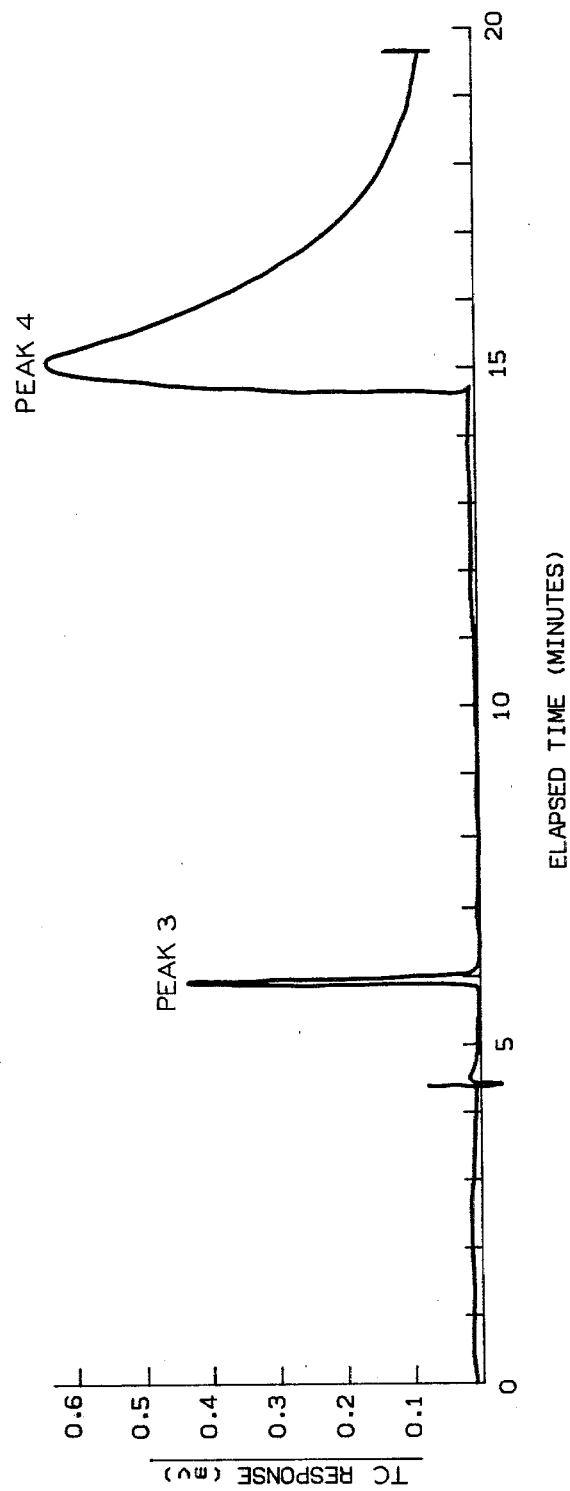
FIG. 7 is a pyrogram showing the charted results of a thermal analysis of a geological sample using the invention injection system and a thermal conductivity detector.

A thermal analysis of a Toarcian Oil Shale sample was performed using the invention in place of the conventional injector of a gas chromatograph. The cas chromatograph contained a calibrated flame ionization detector and a thermal conductivity detector. The specific gas chromatograph of the invention is a Perkin-Elmer Sigma 1 Gas Chromatography System. A Theall Dual Stage Temperature Programmer, Model 2200 and a Perkin-Elmer Model 56 Recorder were also used in this example. FIG. 6 and FIG. 7 are pyrograms charting the detector response in millivolts vs time. The gas chromatograph oven was maintained at a temperature of about 300° C. The FID was operated with a potential difference of 200 volts between the burner tip and the collector screen on a sensitivity range calibrated to a maximum output of 1 millivolt. Helium was used as a carrier gas and the detector was allowed to stabilize using a carrier gas flow of 33 cc/min prior to the insertion of the sample. A crushed and dried sample of a Toarcian oil shale weighing 27.42 milligrams was placed into a 4 by 36 millimeter quartz tube sealed with quartz wool and a quartz frit, sintered screen. Both the tube and the wool have been cleaned with distilled-in-glass reagent grade pure methylene chloride. The sample tube was then placed within the open end of a hollowed out stainless steel sample insertion probe with the sample end of said probe positioned within the sample chamber of the invention sample injector and the sample inlet was sealed. The sample holding chamber was maintained about 60° C. by indirect heat exchange with compressed air flowing in the angular space surrounding the sample containing chamber. A carrier gas was introduced upstream of the sample and allowed to flow across the sample for a period of about 2 minutes to remove entrapped contaminants and to stabilize the detectors. After this initial holding period the sample was heated at a rate of 30° C. per minute to a temperature of 300° C. by the temperature programmer. In this case the effluent from the thermal extraction was split equally, the first part going directly into the FID detector and the response seen as Peak 1 in FIG. 6 and the second part being detected through a $CO_2$ trap and then to the vent. After a total elapse time of approximately 10 minutes a second heating stage is initiated by the temperature programmer at a rise rate of 30° C. per minute and a final temperature of 575° C. Again the effluent was split equally, the first part passing directly into the flame ionization detector, and the response seen as Peak 2 in FIG. 6 and the second part passing through a $CO_2$ trap and to the vent. At a temperature of 400° C., the contents of the trap, a liquid nitrogen containing flask at 180° C., were flushed into a separation column and the remaining effluent released from 400° C. to 575° C. was vented. At the time of the effluent venting above 400° C. the trapped effluent is passed through a ⅛"×6' Parapak Q column to separate the carbon dioxide from the other components and said carbon dioxide was directed to the thermal conductivity detector with the response seen as Peak 3 in FIG. 7. After the elution of Peak 3 the column is backflushed through the detector and was seen as Peak 4 in FIG. 7. The amount of hydrocarbon and carbon dioxide generated from the whole rock kerogen and migration ratio seen as Peak 1 to Peak 2 ratios are calculated from this analysis.

I claim:

1. An injection system adapter for an analytical instrument for analyzing vapors thermally extracted from a sample selected from solids and liquids, the analytical instrument including at least one detecting means and an internal heat source, the injection system adapter comprising a first section comprising a sample chamber, means for heating the sample chamber, a carrier gas inlet to the sample chamber, a sample inlet at one end of the sample chamber and an opposing outlet; and a second ajoining section comprising means for defining a flow path extending from said outlet and for absorbing heat from the internal heat source of the analytical instrument, thereby preventing vapor condensation in said flow path.

2. The adapter of claim 1 in which the means for heating the sample chamber comprises a heating element in physical contact with said first section of the injection system adapter.

3. The adapter of claim 1 in which the means for heating the sample chamber includes means for operatively associating the heating means with a temperature control means.

4. The adapter of claim 3 in which the temperature control means comprises a microprocessor.

5. The adapter of claim 4 in which the temperature control means further comprises a thermocouple in direct contact with a tubular member defining the sample chamber and capable of being operatively associated with the microprocessor.

6. The adapter of claim 1 in which the means for defining a flow path is at least one rigid metal tube.

7. The adapter of claim 6 in which the sample chamber is within a tubular member having an inlet end and an outlet end.

8. The adapter of claim 7 which further comprises a jacket enclosing and spaced apart from at least a portion of the length of the tubular member so as to form an annular space between the tubular member and the jacket.

9. The adapter of claim 7 in which the jacket comprises a fluid inlet to the annular space and a fluid outlet from the annular space.

10. The adapter of claim 1 in which the sample chamber heating means is a heating coil in the first section of the injection system adapter.

11. The adapter of claim 10 which further comprises a thermocouple in close contact with the sample chamber.

12. The adapter of claim 7 which further comprises a guide pin for positioning the adapter within the analytical instrument.

13. The adapter of claim 7 which further comprises a heating coil along and in close contact with at least a portion of the length of the tubular member.

14. The adapter of claim 13 which further comprises a thermocouple in close contact with the tubular member.

15. An analytical instrument for performing a thermal analysis of a sample selected from solids and liquids, the analytical instrument comprising:

detecting means;

a heat source for maintaining the components of the analytical instrument at a predetermined elevated temperature;

a sample injection system in flow communication with the detecting means, the sample injection system comprising a first section comprising a sample chamber, means within the sample injection system for heating the sample chamber, a carrier gas inlet to the sample chamber, a sample inlet at one end of the sample chamber and an opposing carrier gas outlet; and a second adjoining section comprising means for defining a flow path extending from said carrier gas outlet to said detecting means and for absorbing heat from the heat source of the analytical instrument; and means for controlling the temperature of said means for heating the sample chamber.

16. The analytical instrument of claim 15 in which the means for heating the sample chamber comprises a heating element in physical contact with said first section of the injection system adapter.

17. The analytical instrument of claim 15 in which the means for defining a flow path is a rigid metal tube.

18. The analytical instrument of claim 17 in which the sample chamber is within a tubular member having an inlet end and an outlet end, the outlet end extending into the flow path defined by the rigid metal tube.

19. The analytical instrument of claim 18 in which the means for heating the sample chamber is a heating coil around at least a portion of the exterior of the tubular member.

20. The analytical instrument of claim 19 which further comprises a jacket enclosing at least a portion of and spaced apart from the tubular member so as to form an annular space between the tubular member and the jacket, the annular space surrounding the exterior of the sample chamber.

21. The analytical instrument of claim 20 in which the jacket comprises a fluid inlet to the annular space and a fluid outlet from the annular space.

22. The analytical instrument of claim 21 in which the heating coil is physically affixed to at least a portion of the length of the tubular member within the annular space.

23. The analytical instrument of claim 15, 16 or 22 which further comprises temperature-programming means operatively associated with the means for heating the sample chamber.

* * * * *